United States Patent [19]

Hooks, Jr. et al.

[11] 3,992,506

[45] Nov. 16, 1976

[54] PROCESS FOR RECOVERY OF SILVER AND REGENERATION OF 2-MERCAPTOPYRIDINE-1-OXIDE

[75] Inventors: Haywood Hooks, Jr., West Haven; James J. Pitts, Hamden, both of Conn.

[73] Assignee: Olin Corporation, New Haven, Conn.

[22] Filed: June 23, 1975

[21] Appl. No.: 589,293

[52] U.S. Cl. .............................. 423/42; 260/270 K; 260/294.8 R; 210/45; 210/54
[51] Int. Cl.² ............................................ C01G 5/00
[58] Field of Search .................... 260/270 K, 294.8; 423/34, 42, 43, 491; 210/42, 45, 54

[56] References Cited

UNITED STATES PATENTS

| | | | |
|---|---|---|---|
| 2,544,904 | 9/1955 | Steiger | 260/270 K |
| 2,809,971 | 10/1957 | Bernstein et al. | 260/270 K |
| 3,755,158 | 8/1973 | Inazuka | 210/54 R |
| 3,778,368 | 12/1973 | Nakamura | 210/54 R |

*Primary Examiner*—Oscar R. Vertiz
*Assistant Examiner*—Brian E. Hearn
*Attorney, Agent, or Firm*—F. A. Iskander; T. P. O'Day

[57] ABSTRACT

A method is provided for removing silver from aqueous systems contaminated therewith with 2-mercaptopyridine-1-oxide and for recovering the 2-mercaptopyridine-1-oxide.

7 Claims, No Drawings

PROCESS FOR RECOVERY OF SILVER AND REGENERATION OF 2-MERCAPTOPYRIDINE-1-OXIDE

BACKGROUND OF THE INVENTION

The present invention relates to the use of 2-mercaptopyridine-1-oxide as an agent for removing silver from aqueous streams of suspensions and for recovering both the silver and the 2-mercaptopyridine-1-oxide. More particularly, the invention relates to a method for reclamation of silver as its halide and regeneration of 2-mercaptopyridine-1-oxide from aqueous suspensions of the silver salt of 2-mercaptopyridine-1-oxide.

Thus, the present invention is useful for the reclamation of silver in plants producing silver articles, for purifying effluent streams containing silver in preparation for disposal and for numerous other applications where it is desired to remove and/or recover silver from aqueous streams or suspensions thereof.

The heavy metal salts of 2-mercaptopyridine-1-oxide, including the silver salt thereof, are disclosed and claimed in Bernstein, U.S. Pat. No. 2,809,971. Their use as bactericides, fungicides and nematocides is also disclosed therein.

In the present invention the water insoluble silver salt of 2-mercaptopyridine-1-oxide which forms when 2-mercaptopyridine-1-oxide (including its soluble salts) is added to aqueous ionic silver containing systems provides a highly efficient mechanism for removal of silver. But to be of any commercial value, it must also be possible to regenerate 2-mercaptopyridine-1-oxide for reuse in the system or resale.

SUMMARY OF THE INVENTION

We have now found that this may be accomplished by removing the silver salt of 2-mercaptopyridine-1-oxide from the aqueous steam or suspension in which it is formed, for example, by filtration, then reacting the silver salt of 2-mercaptopyridine-1-oxide with hydrochloric acid, separating the silver chloride from resulting suspension, neutralizing the resulting liquid from said suspension and recovering therefrom the 2-mercaptopyridine-1-oxide either as such or as a marketable heavy metal salt thereof.

DETAILED DESCRIPTION

In silver plating of metals, waste plating solutions contain substantial amounts of silver. The silver may be partially removed, for example, by plating it out in decomposition tanks utilizing carbon arcs. However, trace quantities remain and efforts to remove these traces economically have been unsuccessful. The addition of an alkali metal salt of 2-mercaptopyridine-1-oxide results in the formation of the water insoluble silver salt of 2-mercaptopyridine-1-oxide even where only traces of silver are present. The precipitate is readily separated, for example, by filtration or other suitable means.

In accordance with the present invention, the separated silver salt of 2-mercaptopyridine-1-oxide is reacted with hydrochloric acid. The reaction may be conducted at ambient temperature or at a temperature in the range of 15° C. to 100° C., advantageously 25° C. to 75° C. by heating the silver salt with hydrochloric acid. Theoretically, at least 1 mole of hydrochloric acid (100% basis) is required per mole of the silver salt of 2-mercaptopyridine-1-oxide to maximize yields of silver chloride, but more or less may be employed as desired, for example, from 1-15 moles per mole of silver-2-mercaptopyridine-1-oxide. Preferably a molar excess is employed, suitably from 1.01–10 moles per mole of silver-2-mercaptopyridine-1-oxide. Concentrated hydrochloric acid is preferred but less concentrated solutions of HCl may also be employed. The hydrochloric acid readily dissolves silver-2-mercaptopyridine-1-oxide and reacts therewith in accordance with the equation

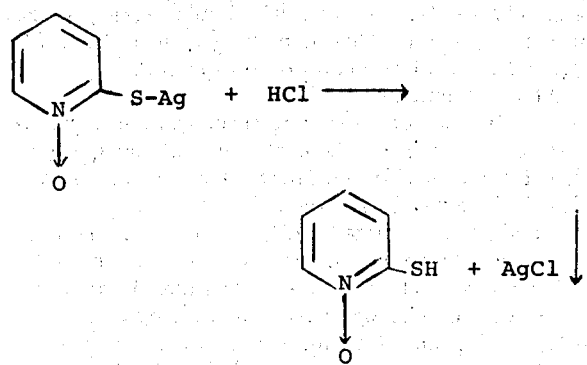

The silver chloride is then separated from the reaction mixture by any known means, for example, by filtration or centrifugation.

The liquor from which the silver chloride is separated contains the 2-mercaptopyridine-1-oxide in solution together with impurities which were not precipitated in the hydrochloric acid reaction step.

To recover the 2-mercaptopyridine-1-oxide from this liquor, the liquor is neutralized to a pH in the range of 3–6, preferably 3–5. The neutralization is advantageously accomplished by adding water, an alkali metal or ammonium hydroxide, carbonate, or bicarbonate or by adding a mixture of these, preferably as an aqueous solution. Water is preferred due to cost factors and to avoid introduction of extraneous ions which could, depending on the contaminants present, cause precipitation of solids other than 2-mercaptopyridine-1-oxide.

Following neutralization, the 2-mercaptopyridine-1-oxide is recovered and at least two means for recovery are contemplated depending on the desired end use. In the preferred embodiment shown in the accompanying example, the neutralized aqueous solution is extracted with a suitable organic solvent, for example, methylene chloride, chloroform or carbon tetrachloride, the phases separated and the organic solvent removed to produce 2-mercaptopyridine-1-oxide per se. This method for recovery is particularly useful where it is desired to regenerate the 2-mercaptopyridine-1-oxide for reuse in precipitating silver as described above. Alternatively, the 2-mercaptopyridine-1-oxide may be recovered following neutralization by adding a soluble heavy metal salt, and recovering the resulting insoluble heavy metal salt of 2-mercaptopyridine-1-oxide as disclosed in U.S. Pat. No. 2,809,971. If this method is employed, it is particularly desirable to utilize a zinc salt and to recover zinc-2-mercaptopyridine-1-oxide which may then be sold as an antimicrobial agent as disclosed in the above-described patent.

The following example is intended to illustrate the invention.

EXAMPLE 1

A 20g sample of the silver salt of 2-mercaptopyridine-1-oxide, previously prepared by reacting aqueous silver nitrate and aqueous sodium-2-mercaptopyridine-1-oxide, was added to 150 ml concentrated hydrochloric acid and heated with stirring to 50° C. for one hour. A white precipitate was filtered off, washed with water and dried to yield 10.8g (87% yield) of silver chloride.

The acidic filtrate from above was diluted with 100 ml of water to raise the pH to slightly above 3. The 2-mercaptopyridine-1-oxide which was present was then extracted with 100 ml of chloroform. The chloroform was finally distilled off under reduced pressure to give 8.5g (77% yield) of 2-mercaptopyridine-1-oxide which was identified by its melting point (73° C.–74° C.) and by its infrared absorption spectrum.

What is claimed is:

1. A process for recovering silver from an aqueous system contaminated therewith with 2-mercaptopyridine-1-oxide and for recovering the 2-mercaptopyridine-1-oxide which comprises:
    a. adding 2-mercaptopyridine-1-oxide to an aqueous system contaminated with silver to form an insoluble silver salt of 2-mercaptopyridine-1-oxide and separating said silver salt from said system;
    b. reacting said silver salt with hydrochloric acid at a temperature in the range of 15° C.–100° C.;
    c. separating the resulting precipitate from the reaction mixture; and
    d. neutralizing the resulting liquid phase of said reaction mixture to a pH in the range of 3 to 5 and recovering 2-mercaptopyridine-1-oxide.

2. The process of claim 1 wherein said temperature is in the range of 25° C.–75° C.

3. The process of claim 1 wherein said silver salt is reacted with concentrated hydrochloric acid.

4. The process of claim 3 wherein at least an equimolar amount of hydrochloric acid based on the amount of silver salt of 2-mercaptopyridine-1-oxide is employed.

5. The process of claim 1 wherein the liquid phase of said suspension is neutralized with water.

6. The process of claim 1 wherein 2-mercaptopyridine-1-oxide is recovered by extracting the neutralized liquid phase with chloroform, separating the resulting aqueous and organic phases and stripping off chloroform.

7. A process for recovering silver as silver chloride and regenerating 2-mercaptopyridine-1-oxide from an aqueous suspension of the silver salt of 2-mercaptopyridine-1-oxide comprising:
    a. separating said silver salt from said suspension;
    b. reacting said silver salt with at least an equimolar amount of hydrochloric acid; at a temperature in the range of 25° C.–75° C.;
    c. separating silver chloride from the resulting suspension; and
    d. neutralizing the resulting liquid phase of said suspension to a pH in the range of 3 to 5 with water and recovering 2-mercaptopyridine-1-oxide.

* * * * *